US012763217B2

(12) United States Patent
Diem et al.

(10) Patent No.: US 12,763,217 B2
(45) Date of Patent: Oct. 13, 2026

(54) COMPUTER IMPLEMENTED METHOD FOR DETERMINING A HEART FAILURE STATUS OF A PATIENT, TRAINING METHOD AND SYSTEM

(71) Applicant: BIOTRONIK SE & Co. KG, Berlin (DE)

(72) Inventors: Bjoern Henrik Diem, Berlin (DE); Antje Linnemann, Berlin (DE); Richard Jordan, Berlin (DE)

(73) Assignee: BIOTRONIK SE & Co. KG, Berlin (DE)

( * ) Notice: Subject to any disclaimer, the term of this patent is extended or adjusted under 35 U.S.C. 154(b) by 0 days.

(21) Appl. No.: 18/710,272

(22) PCT Filed: Nov. 10, 2022

(86) PCT No.: PCT/EP2022/081414
§ 371 (c)(1),
(2) Date: May 15, 2024

(87) PCT Pub. No.: WO2023/088767
PCT Pub. Date: May 25, 2023

(65) Prior Publication Data
US 2025/0014756 A1 Jan. 9, 2025

(30) Foreign Application Priority Data
Nov. 19, 2021 (EP) .................................... 21209295

(51) Int. Cl.
*G16H 50/30* (2018.01)
*A61B 5/00* (2006.01)
(Continued)

(52) U.S. Cl.
CPC ........... *G16H 50/30* (2018.01); *A61B 5/7221* (2013.01); *G16H 10/20* (2018.01); *G16H 10/60* (2018.01); *G16H 40/67* (2018.01); *A61B 5/318* (2021.01)

(58) Field of Classification Search
CPC ........ G16H 50/30; G16H 10/20; G16H 10/60; G16H 40/67; G16H 50/20; G16H 50/70; G16H 40/63; A61B 5/7221; A61B 5/318
(Continued)

(56) References Cited

U.S. PATENT DOCUMENTS 7,801,591 B1 * 9/2010 Shusterman ......... A61B 5/7264 600/509
11,837,364 B2 * 12/2023 Lee ........................ G16H 10/60
2021/0125722 A1 * 4/2021 Sherkat .................... G06N 3/04

FOREIGN PATENT DOCUMENTS

WO WO-2021022003 A1 * 2/2021 ........... A61B 5/4833

OTHER PUBLICATIONS

Patel et al., Machine learning for predicting cardiac events: what does the future hold? Expert review of cardiovascular therapy, Feb. 23, 2020, 18(2), 77-84. https://doi.org/10.1080/14779072.2020.1732208 (Year: 2020).*

(Continued)

*Primary Examiner* — Joy Chng
(74) *Attorney, Agent, or Firm* — Buchanan Ingersoll & Rooney PC

(57) ABSTRACT

A computer-implemented method for determining a heart failure status of a patient, comprising the steps of providing a first data set comprising cardiac current curve data of a patient acquired by an implantable medical device, applying a first machine learning algorithm and/or a rule-based algorithm to the cardiac current curve data for classification of a medical relevance of a parameter deviation from a norm of the cardiac current curve data, and applying a second
(Continued)

machine learning algorithm to the third data set for determining the heart failure status of the patient. In addition, the invention relates to a corresponding system and methods for providing a first and second trained machine learning algorithm respectively.

13 Claims, 2 Drawing Sheets

(51) Int. Cl.

| | |
|---|---|
| ***A61B 5/318*** | (2021.01) |
| ***G16H 10/20*** | (2018.01) |
| ***G16H 10/60*** | (2018.01) |
| ***G16H 40/67*** | (2018.01) |

(58) Field of Classification Search
USPC .......................................................... 705/2-3
See application file for complete search history.

(56) References Cited

OTHER PUBLICATIONS

Segar et al., Machine Learning to Predict the Risk of Incident Heart Failure Hospitalization Among Patients With Diabetes: The WATCH-DM Risk Score. Diabetes Care. Sep. 13, 2019; 42(12):2298-2306. doi: 10.2337/dc19-0587 (Year: 2019).*

International Search Report (PCT/ISA/210) and Written Opinion (PCT/ISA/237) mailed Feb. 15, 2023, by the European Patent Office as the International Searching Authority for International Application No. PCT/EP2022/081414. (8 pages).

* cited by examiner

COMPUTER IMPLEMENTED METHOD FOR DETERMINING A HEART FAILURE STATUS OF A PATIENT, TRAINING METHOD AND SYSTEM

CROSS-REFERENCE TO RELATED APPLICATIONS

This application is the United States National Phase under 35 U.S.C. § 371 of PCT International Patent Application No. PCT/EP2022/081414, filed on Nov. 10, 2022, which claims the benefit of European Patent Application No. 21209295.1, filed on Nov. 19, 2021, the disclosures of which are hereby incorporated by reference herein in their entireties.

TECHNICAL FIELD

The present invention relates to a computer-implemented method for determining a heart failure status of a patient.

BACKGROUND

Furthermore, the present invention relates to a computer implemented method for providing a first trained machine learning algorithm configured to classify a medical relevance of a parameter deviation from a norm of (pre-acquired) cardiac current curve data.

Moreover, the present invention relates to a computer implemented method for providing a second trained machine learning algorithm configured to determine a heart failure status of a patient.

In addition, the present invention relates to a system for determining a heart failure status of a patient.

Many diseases of the heart are accompanied by changes in the ECG. These could be detected at an early stage by close-meshed ECG checks. However, this is logistically not feasible in everyday life.

Conventionally, said ECG is recorded at after care visits of the patient having an implantable medical device at a health provider, such after care visits typically being scheduled every 1 to 3 months. To this end, a twelve-channel ECG is recorded at the health providers site. The recording of a conventional twelve-channel ECG is however associated with a relevant expenditure of time and personnel. Alternatively, remote transmission of a twelve-channel ECG requires the active cooperation and compliance of the patient, who may be overtaxed.

International Publication No. WO 2021/022003 A1 discloses a system for managing an individualized cardiac rehabilitation plan. The system includes an externally worn device and a server. The server includes a processor configured to receive input regarding the rehabilitation plan, generate one or more plans specifying an individualized set of rehabilitative exercise sessions for a patient, receive electrocardiogram (ECG) and non-ECG physiological information acquired from the patient, compare the ECG and/or non-ECG physiological information to predetermined criteria and dynamically adjust the cardiac rehabilitation plan based on the comparison to create an adjusted cardiac rehabilitation plan.

The present disclosure is directed toward overcoming one or more of the above-mentioned problems, though not necessarily limited to embodiments that do.

SUMMARY

It is therefore an object of the present invention to provide an improved method for automated remote monitoring of cardiac current curves for evaluating a heart failure status of a patient with higher frequency and accuracy than possible by outpatient follow-up.

At least the object is solved by a computer implemented method for determining a heart failure status of a patient.

Furthermore, at least the object is solved by a computer implemented method for providing a first trained machine learning algorithm configured to classify a medical relevance of a parameter deviation from a norm of (pre-acquired) cardiac current curve data.

Moreover, at least the object is solved by a computer implemented method for providing a second trained machine learning algorithm configured to determine a heart failure status of a patient. In addition, at least the object is solved by a system for determining a heart failure status of a patient.

Further developments and advantageous embodiments are defined in the dependent claims.

The present invention provides a computer implemented method for determining a heart failure status of a patient.

The method comprises providing a first data set comprising cardiac current curve data of a patient acquired by an implantable medical device and applying a first machine learning algorithm and/or a rule-based algorithm to the (pre-acquired) cardiac current curve data for classification of a medical relevance of a parameter deviation from a norm of the (pre-acquired) cardiac current curve data.

Cardiac current curve data of a patient acquired by an implantable medical device may also be referred to as pre-acquired cardiac current curve data below.

Furthermore, the method comprises outputting a second data set comprising at least a first class representing a medically relevant parameter deviation or a second class representing a medically not relevant parameter deviation, and in response to outputting the second class, triggering a patient information request.

In addition, the method comprises providing a third data set comprising the first data set and data provided in response to the patient information request, applying a second machine learning algorithm to the third data set for determining the heart failure status of the patient, and outputting a fourth data set indicative of the heart failure status of a patient.

Furthermore, the present invention provides a computer implemented method for providing a first trained machine learning algorithm configured to classify a medical relevance of a parameter deviation from a norm of the (pre-acquired) cardiac current curve data.

The method comprises receiving a first training data set comprising first cardiac current curve data of a patient acquired by an implantable medical device and receiving a second training data set comprising at least a first class representing a medically relevant parameter deviation or a second class representing a medically not relevant parameter deviation.

Moreover, the method comprises training the first machine learning algorithm by an optimization algorithm which calculates an extreme value of a loss function for classification of the first class representing the medically relevant parameter deviation or the second class representing the medically not relevant parameter deviation.

Furthermore, the present invention provides a computer implemented method for providing a second trained machine learning algorithm configured to determine a heart failure status of a patient.

The method comprises receiving a first training data set comprising a first data set and data provided in response to a patient information request and receiving a second training data set indicative of the heart failure status of a patient. Moreover, the method comprises training the second machine learning algorithm by an optimization algorithm which calculates an extreme value of a loss function for determining the heart failure status of the patient.

In addition, the present invention provides a system for determining a heart failure status of a patient comprising an implantable medical device for acquiring a first data set comprising cardiac current curve data of a patient and means for applying a first machine learning algorithm and/or a rule-based algorithm to the (pre-acquired) cardiac current curve data for classification of a medical relevance of a parameter deviation from a norm of the (pre-acquired) cardiac current curve data.

The system further comprises means for outputting a second data set comprising at least a first class representing a medically relevant parameter deviation or a second class representing a medically not relevant parameter deviation, and in response to outputting the first and/or second class, triggering a patient information request. The patient information request may be triggered by the medically relevant parameter deviation. Preferably, the first class may trigger the patient information request R.

Moreover, the system comprises means for providing a third data set comprising the first data set and data provided in response to the patient information request, means for applying a second machine learning algorithm to the third data set for determining the heart failure status of the patient, and means for outputting a fourth data set indicative of the heart failure status of a patient.

An idea of the present invention is to provide automatic remote monitoring of a heart failure status by combining data from active implanted cardiac implants with symptom questionnaires collected by smartphones and other external data. Data from the active implant will be used to prompt the patient to complete the questionnaire via, e.g., a smartphone. The patient's current heart failure status can thus be assessed based on the overall view of the data and alerting the attending physician and nurses to relevant changes in heart failure status.

Specifically, the system requests additional information from the patient via his smartphone when there is an initial suspicion of a change in heart failure status. This is done automatically and without any intervention by the physician. The system then determines the patient's exact heart failure status, also fully automatically. In the event of relevant deviations, the physician is informed. This also gives the physician initial information directly from the patient on what is currently happening and allows to assess more quickly whether the event requires intervention. The system also enables to inform the patient directly via a corresponding smartphone app without having to call the patient.

Combining implant data with data queried from the patient increases specificity reducing the number of false alarms and the workload of the physician who can focus on clinically important alarms. Thus, an improvement of therapy quality through early detection of changes in a patient's heart failure status can be provided.

Machine learning algorithms are based on using statistical techniques to train a data processing system to perform a specific task without being explicitly programmed to do so. The goal of machine learning is to construct algorithms that can learn from data and make predictions. These algorithms create mathematical models that can be used, for example, to classify data or to solve regression type problems.

According to an aspect of the present invention, the fourth data set comprises at least a third class representing a normal heart failure status of the patient and a fourth class representing an abnormal heart failure status of the patient and/or wherein the fourth data set comprises a numerical value or a categorical value indicative of the heart failure status of the patient. Thus, the first machine learning algorithm can advantageously based on the cardiac current curve data determine whether or not further patient information needs to be requested.

According to a further aspect of the present invention, the patient information request is sent to a user communication device and/or smartphone, and wherein the patient is prompted to input information, in particular a body weight and/or symptoms, and/or information is imported from an app installed on the user communication device and/or the smartphone. The patient can thus enhance the data set acquired by the implantable medical device by providing further (e.g., subjective) information in relation to symptoms, medical parameters and/or other data available to the patient.

According to a further aspect of the present invention, the information provided by the patient and/or imported from the app installed on the user communication device and/or the smartphone is given by at least one numerical value associated with the body weight of the patient and/or an evaluation of symptoms, answers to multiple-choice questions, and/or text-based answers submitted in text fields. Thus, the patient information is given by quantifiable parameters suitable for evaluation by the second machine learning algorithm.

According to a further aspect of the present invention, in response to outputting the fourth class representing the abnormal heart failure status of the patient, a notification is sent to a communication device of a health care provider. The healthcare provider is thus advantageously informed as soon as the abnormal heart failure status of the patient is detected therefore enabling effective treatment of the patient's condition.

According to a further aspect of the present invention, if the numerical value or the categorical value indicative of the heart failure status of the patient is outside a predetermined range, exceeds or falls below a predetermined threshold value, a notification is sent to a communication device of a health care provider. Said range and/or threshold value can advantageously be set according to predetermined parameters specific to the patient, e.g., based on a medical history of said patient and/or a generally normal range for similar patients.

According to a further aspect of the present invention, the notification and/or heart the failure status of the patient is accessible via a front-end application on/or the communication device, in particular a smart phone and/or a personal computer, of the health care provider. This provides ease of use for the healthcare provider as the communication device is preferably portable such that the information can be accessed by the healthcare provider anywhere at any time.

According to a further aspect of the present invention, the second data set outputted by the first machine learning algorithm (and may be by the second machine learning algorithm) and the fourth data set outputted by the second machine learning algorithm are stored on the central server and are accessible by the front-end application on/or the communication device of the health care provider. The healthcare provider thus has a wide range of information and/or data sources available for review should it be necessary.

According to a further aspect of the present invention, providing the third data set comprises providing the first data set stored on a central server and providing the data supplied in response to the patient information request via the user communication device and/or the smartphone of the patient. The third data set thus advantageously comprises data from two different sources thus enhancing the accuracy with which the heart failures status of the patient can be determined.

According to a further aspect of the present invention, the first data set further comprises arrhythmia data, a heart rate, a patient activity, a chest impedance, and/or readings from electrodes of the implantable medical device. Said multiple data types advantageously provide a more accurate analysis and/or determination of the heart failures status of the patient.

According to a further aspect of the present invention, the cardiac current curve data is acquired by the implantable medical device at predetermined intervals and/or on request, and wherein the cardiac current curve data is transmitted to a central server via a patient communication device or smartphone. Said intervals can advantageously be set according to specific patient requirements and/or requirements set by a medical practitioner of the healthcare provider.

The herein described features of the system for determining a heart failure status of a patient are also disclosed for the computer implemented method for determining a heart failure status of a patient and vice versa.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

For a more complete understanding of the present invention and advantages thereof, reference is now made to the following description taken in conjunction with the accompanying drawings. The present invention is explained in more detail below using exemplary embodiments, which are specified in the schematic figures of the drawings, in which.

DETAILED DESCRIPTION

Figure 1:
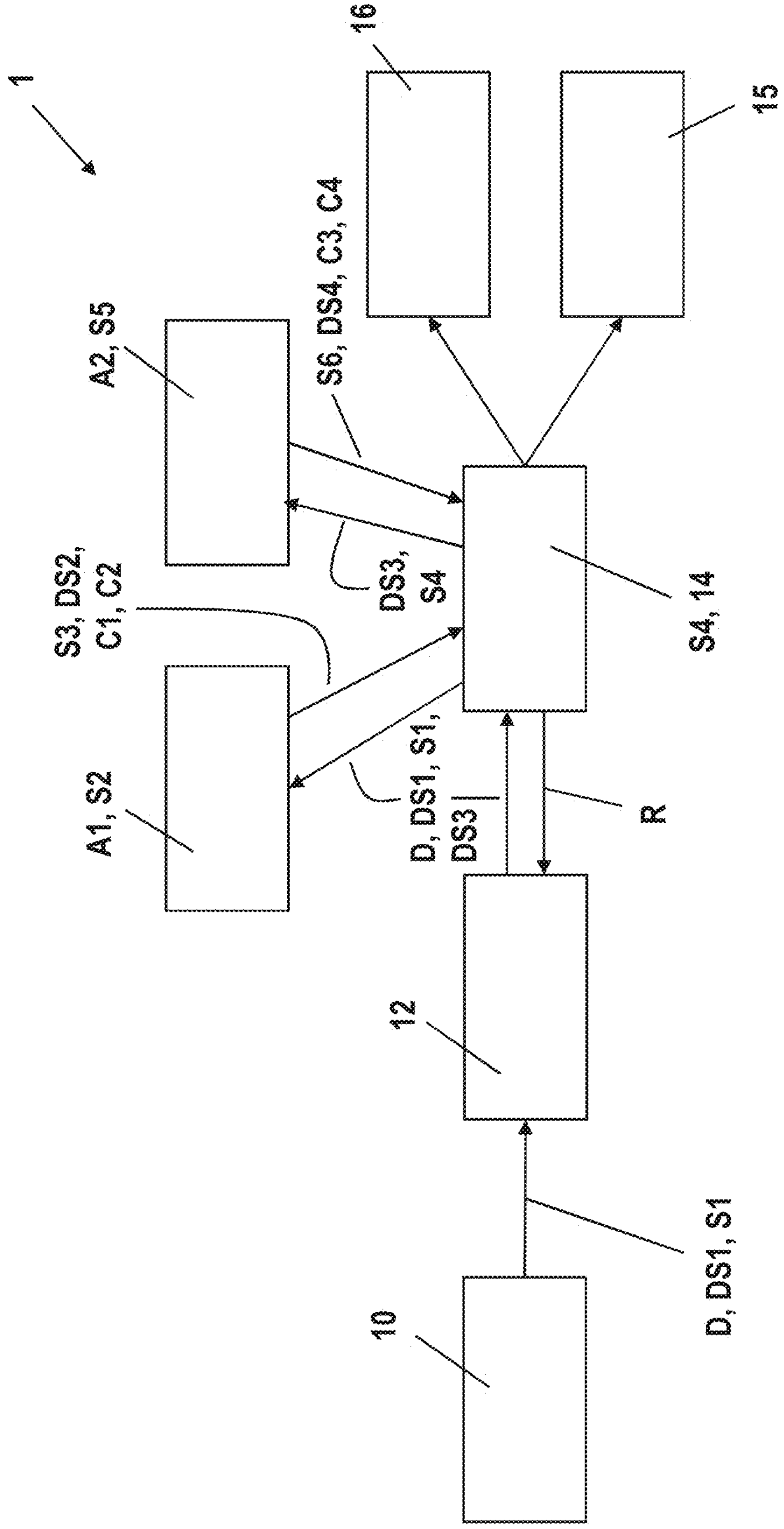
FIG. 1 shows a flowchart of a computer implemented method and system for determining a heart failure status of a patient according to a preferred embodiment of the present invention.

The system 1 shown in FIG. 1 for determining a heart failure status of a patient, comprises an implantable medical device 10 for acquiring S1 a first data set DS1 comprising cardiac current curve data D of a patient.

Furthermore, the system comprises means for applying S2 a first machine learning algorithm A1 and/or a rule-based algorithm to the (pre-acquired) cardiac current curve data D for classification of a medical relevance of a parameter deviation from a norm of the (pre-acquired) cardiac current curve data D and means for outputting S3 a second data set DS2 comprising at least a first class C1 representing a medically relevant parameter deviation or a second class C2 representing a medically not relevant parameter deviation.

In addition, the system comprises in response to outputting the first class C1 and/or the second class C2 triggering S4 a patient information request R. The system further comprises means for providing S1 a third data set DS3 comprising the first data set DS1 and data provided in response to the patient information request R, means for applying S5 a second machine learning algorithm A2 to the third data set DS3 for determining the heart failure status of the patient, and means for outputting S6 a fourth data set DS4 indicative of the heart failure status of a patient.

The fourth data set DS4 comprises at least a third class C3 representing a normal heart failure status of the patient and a fourth class C4 representing an abnormal heart failure status of the patient and/or wherein the fourth data set DS4 comprises a numerical or categorical value indicative of the heart failure status of the patient.

Furthermore, the patient information request R is sent to a user communication device 12 and/or smartphone, and wherein the patient is prompted to input information, in particular a body weight and/or symptoms, and/or information is imported from an app installed on the user communication device 12 and/or the smartphone.

The information provided by the patient and/or imported from the app installed on the user communication device 12 and/or the smartphone is given by at least one numerical value associated with the body weight of the patient and/or an evaluation of symptoms, answers to multiple-choice questions, and/or text-based answers submitted in text fields.

In response to outputting the fourth class C4 representing the abnormal heart failure status of the patient, a notification is sent to a communication device 16 of a health care provider. Moreover, if the numerical value indicative of the heart failure status of the patient is outside a predetermined range, exceeds or falls below a predetermined threshold value, a notification is sent to a communication device 16 of a health care provider.

The notification and/or heart the failure status of the patient is accessible via a front-end application 15 on/or the communication device, in particular a smart phone and/or a personal computer, of the health care provider. Further, the second data set DS2 outputted by the first machine learning algorithm A1 (and maybe by the second machine learning algorithm A2) and the fourth data set DS4 outputted by the second machine learning algorithm A2 are stored on the central server 14 and are accessible by the front-end application 15 on/or the communication device 16 of the health care provider.

Providing S1 (or S5 or A2) the third data set DS3 further comprises providing the first data set DS1 stored on a central server 14 and providing the data supplied in response to the patient information request R via the user communication device 12 and/or the smartphone of the patient. The first data set DS1 further comprises arrhythmia data, a heart rate, a patient activity, a chest impedance, and/or readings from electrodes of the implantable medical device.

The cardiac current curve data D is acquired by the implantable medical device 10 at predetermined intervals and/or on request. Further, the cardiac current curve data D is transmitted to the central server 14 via a patient communication device or smartphone.

Figure 2:
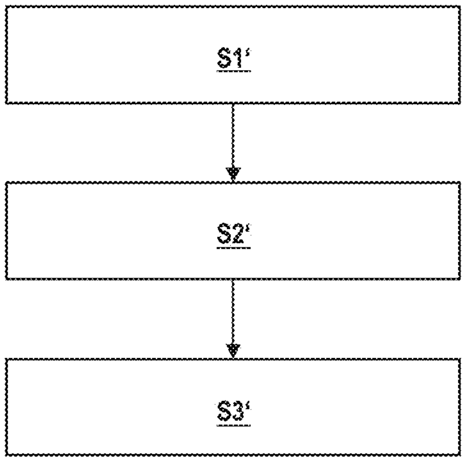
FIG. 2 shows a flowchart of a computer implemented method for providing a first trained machine learning algorithm configured to determine a heart failure status of a patient according to the preferred embodiment of the present invention.

FIG. 2 shows a flowchart of a computer implemented method for providing a first trained machine learning algorithm configured to determine a heart failure status of a patient according to the preferred embodiment of the present invention.

The method comprises receiving S1' a first training data set comprising first cardiac current curve data D of a patient acquired by an implantable medical device 10 and receiving S2' a second training data set comprising at least a first class C1 representing a medically relevant parameter deviation or a second class C2 representing a medically not relevant parameter deviation.

Moreover, the method comprises training S3' the first machine learning algorithm A1 by an optimization algorithm which calculates an extreme value of a loss function for classification of the first class C1 representing the medically relevant parameter deviation or the second class C2 representing the medically not relevant parameter deviation.

Figure 3:
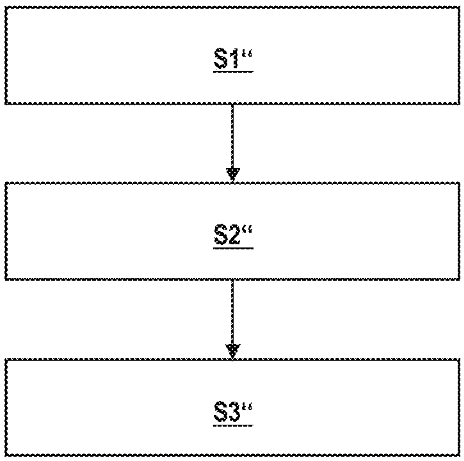
FIG. 3 shows a flowchart of a computer implemented method for providing a second trained machine learning algorithm configured to determine a heart failure status of a patient according to the preferred embodiment of the present invention.

FIG. 3 shows a flowchart of a computer implemented method for providing a second trained machine learning algorithm configured to determine a heart failure status of a patient according to the preferred embodiment of the present invention.

The method comprises receiving S1" a first training data set comprising a first data set DS1 and data provided in response to a patient information request R and receiving S2" a second training data set indicative of the heart failure status of a patient.

Furthermore, the method comprises training S3" the second machine learning algorithm A2 by an optimization algorithm which calculates an extreme value of a loss function for determining the heart failure status of the patient.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

REFERENCE SIGNS

1 system
10 implantable medical device
12 user communication device
14 central server
15 front-end application
16 communication device of health care provider
A1 first machine learning algorithm
A2 second machine learning algorithm
C1 first class
C2 second class
C3 third class
C4 fourth class
D cardiac current curve data
DS1 first data set
DS2 second data set
DS3 third data set
DS4 fourth data set
R patient information request
S1-S6 method steps
S1'-S3' method steps
S1"-S3" method steps

The invention claimed is:

1. Computer-implemented method for determining a heart failure status of a patient, comprising the steps of:

providing a first data set comprising cardiac current curve data of a patient acquired by an implantable medical device;

applying a first machine learning algorithm and/or a rule-based algorithm to the cardiac current curve data for classification of a medical relevance of a parameter deviation from a norm of the cardiac current curve data;

outputting a second data set comprising at least a first class representing a medically relevant parameter deviation or a second class representing a medically not relevant parameter deviation;

in response to outputting the first class, triggering a patient information request;

providing a third data set comprising the first data set and data provided in response to the patient information request;

applying a second machine learning algorithm to the third data set for determining the heart failure status of the patient; and outputting a fourth data set indicative of the heart failure status of a patient.

2. Computer-implemented method of claim 1, wherein the fourth data set comprises at least a third class representing a normal heart failure status of the patient and a fourth class representing an abnormal heart failure status of the patient and/or wherein the fourth data set comprises a numerical value indicative of the heart failure status of the patient.

3. Computer-implemented method of claim 2, wherein in response to outputting the fourth class representing the abnormal heart failure status of the patient, a notification is sent to a communication device of a health care provider.

4. Computer-implemented method of claim 3, wherein the notification and/or heart the failure status of the patient is accessible via a front-end application on/or the communication device, in particular a smart phone and/or a personal computer, of the health care provider.

5. Computer-implemented method of claim 4, wherein the second data set outputted by the first machine learning algorithm and the fourth data set outputted by the second machine learning algorithm are stored on a central server and are accessible by the front-end application on/or the communication device of the health care provider.

6. Computer-implemented method of claim 2, wherein if the numerical value indicative of the heart failure status of the patient is outside a predetermined range, exceeds or falls below a predetermined threshold value, a notification is sent to a communication device of a health care provider.

7. Computer-implemented method of claim 1, wherein the patient information request is sent to a user communication device and/or smartphone, and wherein the patient is prompted to input information, in particular a body weight and/or symptoms, and/or information is imported from an app installed on the user communication device and/or the smartphone.

8. Computer-implemented method of claim 7, wherein the information provided by the patient and/or imported from the app installed on the user communication device and/or the smartphone is given by at least one numerical value associated with the body weight of the patient and/or an evaluation of symptoms, answers to multiple-choice questions, and/or text-based answers submitted in text fields.

9. Computer-implemented method of claim 1, wherein providing the third data set comprises providing the first data set stored on a central server and providing the data supplied in response to the patient information request via the user communication device and/or the smartphone of the patient.

10. Computer-implemented method of claim 1, wherein the first data set further comprises arrhythmia data, a heart rate, a patient activity, a chest impedance, and/or readings from electrodes of the implantable medical device.

11. Computer-implemented method of claim 1, wherein the cardiac current curve data is acquired by the implantable medical device at predetermined intervals and/or on request, and wherein the cardiac current curve data is transmitted to a central server via a patient communication device or smartphone.

12. System for determining a heart failure status of a patient, comprising:

an implantable medical device for acquiring a first data set comprising cardiac current curve data of a patient;

means for applying a first machine learning algorithm and/or a rule-based algorithm to the cardiac current curve data for classification of a medical relevance of a parameter deviation from a norm of the cardiac current curve data;

means for outputting a second data set comprising at least a first class representing a medically relevant parameter deviation or a second class representing a medically not relevant parameter deviation;

in response to outputting the first class, triggering a patient information request;

means for providing a third data set comprising the first data set and data provided in response to the patient information request;

means for applying a second machine learning algorithm to the third data set for determining the heart failure status of the patient; and means for outputting a fourth data set indicative of the heart failure status of a patient.

13. Computer program with program code to perform the method of claim 1 when the computer program is executed on a computer.

* * * * *